(12) United States Patent
Knott et al.

(10) Patent No.: US 9,562,883 B2
(45) Date of Patent: Feb. 7, 2017

(54) BREATH ALCOHOL TESTER CALIBRATION STATION

(71) Applicant: Lifeloc Technologies, Inc., Wheat Ridge, CO (US)

(72) Inventors: Barry Knott, Wheat Ridge, CO (US); Kelly Silverman, US, CO (US); Mark Lary, Littleton, CO (US); Gurumurthi Ravishankar, Englewood, CO (US)

(73) Assignee: Lifeloc Technologies, Inc., Wheatridge, CO (US)

( * ) Notice: Subject to any disclaimer, the term of this patent is extended or adjusted under 35 U.S.C. 154(b) by 431 days.

(21) Appl. No.: 13/957,180

(22) Filed: Aug. 1, 2013

(65) Prior Publication Data

US 2014/0041436 A1  Feb. 13, 2014

Related U.S. Application Data (60) Provisional application No. 61/680,325, filed on Aug. 7, 2012, provisional application No. 61/759,022, filed on Jan. 31, 2013.

(51) Int. Cl.
  *G01N 33/00*  (2006.01)
  *G01N 33/497* (2006.01)

(52) U.S. Cl.
  CPC ...... *G01N 33/0008* (2013.01); *G01N 33/4972* (2013.01)

(58) Field of Classification Search
  CPC .................. G01N 33/0008; G01N 33/0006
  See application file for complete search history.

(56) References Cited

U.S. PATENT DOCUMENTS

| | | | |
|---|---|---|---|
| 4,749,553 A | 6/1988 | Lopez et al. | |
| 5,443,794 A * | 8/1995 | Williams | G01N 33/4972 422/84 |
| 6,096,558 A | 8/2000 | Stock | |
| 6,442,639 B1 | 8/2002 | McElhattan et al. | |
| 7,543,472 B2 * | 6/2009 | Crespo | G01N 33/4972 73/1.06 |
| D708,757 S | 7/2014 | Shibata | |
| 2003/0000281 A1 | 1/2003 | Ketler et al. | |
| 2003/0167821 A1 | 9/2003 | Sussman et al. | |
| 2007/0044534 A1 | 3/2007 | Forrest | |
| 2009/0056408 A1 * | 3/2009 | Tryfonos | G05D 16/04 73/1.06 |
| 2010/0223975 A1 * | 9/2010 | Lueck | G01N 33/4972 73/1.06 |

FOREIGN PATENT DOCUMENTS

WO  WO 97/14947  *  4/1997  .............. G01N 1/00

OTHER PUBLICATIONS

European Patent Office, European Search Report, Oct. 20, 2015, 5 pages.

* cited by examiner

*Primary Examiner* — Daniel S Larkin
*Assistant Examiner* — Jamar Ray
(74) *Attorney, Agent, or Firm* — Holzer Patel Drennan (57) ABSTRACT

A breath alcohol tester calibration station provides a user-friendly system and method for calibrating a breath alcohol tester with a much lower error rate than current systems and methods for calibrating breath alcohol testers. The calibration station includes a data connection to the breath alcohol tester and a fluid connection between the breath alcohol tester and a calibration standard. The calibration station is used to execute calibration processes on the breath alcohol tester using the calibration standard.

28 Claims, 4 Drawing Sheets

BREATH ALCOHOL TESTER CALIBRATION STATION

CROSS-REFERENCE TO RELATED APPLICATIONS

The present application claims benefit of priority to U.S. Provisional Patent Application No. 61/680,325, entitled "Breath Alcohol Tester Calibration Station" and filed on Aug. 7, 2012, which is specifically incorporated by reference herein for all that it discloses or teaches. The present application also claims benefit of priority to U.S. Provisional Patent Application No. 61/759,022, entitled "Breath Alcohol Tester Calibration Station" and filed on Jan. 31, 2013, which is specifically incorporated by reference herein for all that it discloses or teaches.

BACKGROUND

A breath alcohol tester is a device for estimating a blood alcohol content (BAC) of a user by analyzing a sample of the user's breath. Typically, the user exhales into the breath alcohol tester and any ethanol present in the user's breath is oxidized to yield acetic acid and hydrogen at an anode of the breath alcohol tester. Further, the hydrogen reacts with atmospheric oxygen to yield water at a cathode of the breath alcohol tester. This chemical reaction produces an electric current between the anode and the cathode and a sensor (and associated circuitry) within the breath alcohol tester measures the magnitude of the electric current. The breath alcohol tester outputs an approximation (or representation) of the user's BAC based on the measured electric current.

The anode, cathode, sensor, or other components of the breath alcohol tester may be prone to contamination and interference from substances other than breath alcohol. Further, over time, sensor aging, humidity, and contamination can alter the output of the breath alcohol tester. As a result, the breath alcohol tester may require regular calibration checks or recalibration (collectively calibration processes) to ensure that the breath alcohol tester outputs an accurate estimation (or representation) of BAC. Further, even if the breath alcohol tester does not require regular calibration for accuracy, regular calibration and/or calibration checks of the breath alcohol tester may be required to comply with equipment limitations and/or applicable administrative or legal (e.g., Federal, State, and Local) laws and regulations, for example. There may be other factors that cause the need for regular calibration checks or recalibration of the breath alcohol tester.

Calibration of the breath alcohol tester may be performed using a Dry-Gas method, for example, although other calibration methods are contemplated herein. The Dry-Gas method utilizes a calibration standard, which is a precise mixture of alcohol and inert nitrogen available in a portable pressurized canister. The breath alcohol tester is connected to the calibration standard and measures the alcohol content of the calibration standard. The measured alcohol content is compared with the known alcohol content of the calibration standard. The calibration of the breath alcohol tester is adjusted, if necessary, to match the alcohol content of the calibration standard within a desired degree of accuracy (e.g., within (0.005%).

Calibration of the breath alcohol tester may require specially trained users to accurately and consistently calibrate the breath alcohol tester. Further, if the trained users do not perform the calibration regularly, the users may avoid performing the calibration, induce errors in the calibration, and/or forget how to do the calibration and become uncomfortable performing the calibration. Still further, a failure to correctly calibrate the breath alcohol tester (or not calibrate the breath alcohol tester at all) may render the results obtained from the breath alcohol tester invalid.

SUMMARY

Implementations described and claimed herein address the foregoing problems by providing a method of performing a calibration process on a breath alcohol tester using a calibration station comprising establishing a data connection between the breath alcohol tester and the calibration station; executing the calibration process on the breath alcohol tester; and opening a fluid connection between the breath alcohol tester and a calibration standard in response to execution of the calibration process.

Implementations described and claimed herein address the foregoing problems by further providing a calibration station comprising circuitry configured to establish a data connection between a breath alcohol tester and the calibration station; a calibration fluid interface configured to fluidly connect a calibration standard to the breath alcohol tester; and a valve configured to open the fluid connection between the calibration station and the breath alcohol tester in response to execution of a calibration process on the breath alcohol tester.

Other implementations are also described and recited herein.

DETAILED DESCRIPTIONS

Figure 1:
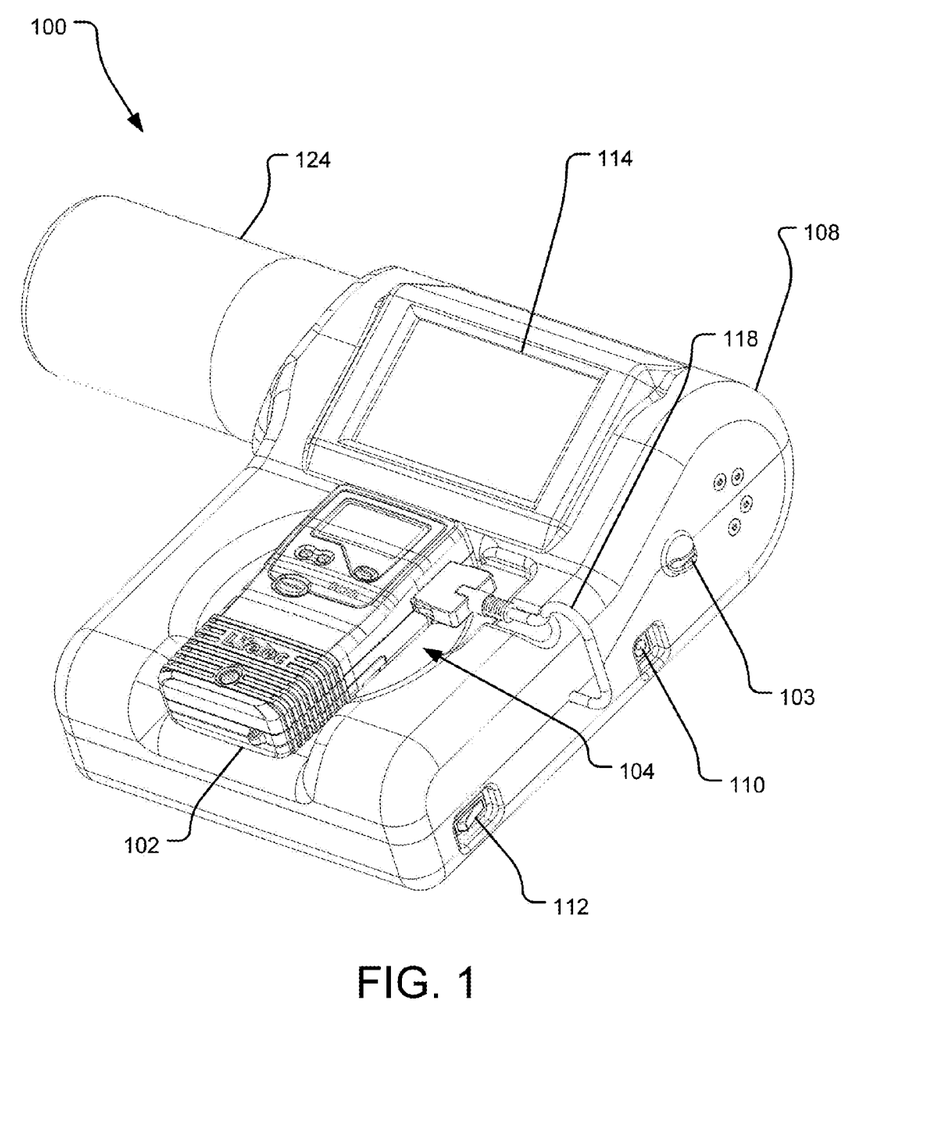
FIG. 1 is a first perspective view of an example calibration station with a breath alcohol tester and a calibration standard mounted thereon.

FIG. 1 is a first perspective view of an example calibration station 100 with a breath alcohol tester 102 mounted thereon. The breath alcohol tester 102 is selectively mounted to the calibration station 100 using a device dock 104 (alternatively referred to herein as a docking station, receiving station, or mounting interface). This fluidly connects the breath alcohol tester 102 to a calibration standard 124 via one or more tubes, hoses, regulators, and/or valves (collectively, a calibration fluid interface, not shown). The calibration standard 124 is a pressurized fluid containing a precise known mixture of alcohol (e.g., ethanol) and inert nitrogen. In various implementations, the ethanol content of the calibration standard 124 is less than about 1100 parts per million.

The breath alcohol tester 102 is placed into the device dock 104 and held in place via a friction, snap, or slip fit, for example. Further, gravitational or other forces may aid in keeping the breath alcohol tester 102 secured within the device dock 104. In other implementations, the device dock 104 is equipped with an ejection button or slider (not shown) for facilitating removal of the breath alcohol tester 102 from the device dock 104. In other implementations, the calibration station 100 does not include a device dock 104. In those implementations, the fluid connection between the breath alcohol tester 102 and the calibration standard 124 may be made by connecting a hose extending from the calibration standard 124 directly to the breath alcohol tester 102, or vice versa.

The calibration station 100 includes a housing 108, which encloses internal components (e.g., a portion of the calibration standard 124, associated hose(s) and valve(s), power supply circuitry, communications circuitry, sensing circuitry, batteries, etc.) of the calibration station 100 (not shown). In one implementation, the housing 108 includes an access door (not shown) that may be removed or opened to access the internal components of the calibration station 100. The access door may be removably attached to a remainder of a housing 108 of the calibration station 100 using a slip-fit, screwed, sliding, or other removable connection.

The calibration standard 124 may take the form of a precise known mixture of alcohol and an inert substance (e.g., nitrogen) stored within a compressed canister, as shown in FIG. 1. The calibration standard 124 may connect to one or more valves and regulators stored within the housing 108, which selectively meter fluid from the calibration standard 124, through one or more tubes hoses, to a calibration fluid interface (not shown, see e.g., FIG. 3) of the breath alcohol tester 102. The valves and regulators may be automatically actuated via user input control to the calibration station 100 and/or the breath alcohol tester 102. In another implementation, the valves and regulators are automatically actuated without user input control. The calibration standard 124 is inserted into an aperture (not shown) in the device dock 104 and screwed or otherwise secured in place and fluidly connected to the breath alcohol tester 102. The user may unscrew the calibration standard 124 when it is empty or nearly empty from a valve and regulator assembly within the calibration station 100 and replace the calibration standard 124 with a new calibration standard. The new calibration standard is screwed back into the valve and regulator assembly.

The sensing circuitry (not shown) may include one or more pressure sensors, mass flow rate sensors, and/or temperature sensors. A pressure sensor may detect the ambient pressure in the surrounding environment and adjust calibration settings of the calibration station 100 and/or the breath alcohol tester 102 accordingly. Further, a pressure sensor may detect the pressure within the calibration standard 124 to determine its state of fill. A mass flow rate sensor may determine the mass flow rate of calibration fluid exiting the calibration standard 124 to accurately meter the fluid and/or determine the state of fill of the calibration standard 124. A mass flow rate sensor may also detect a leaking calibration standard 124. Then, the calibration station 100 may alert the user to adjust the calibration standard 124 mounting or that the calibration station 100 needs service. A temperature sensor may detect the temperature of the calibration fluid exiting the calibration standard 124 and adjust the calibration settings accordingly. The sensing circuitry may include multiple pressure sensors, mass flow rate sensors, and/or temperature sensors for redundancy purposes.

The calibration station 100 includes a power supply port 110 with which a user may connect a power supply cord (not shown) to directly power the calibration station 100 and/or charge one or more batteries (not shown) within the calibration station 100. Further, the power supply port 110 may be used to directly power the breath alcohol tester 102 and/or charge one or more batteries within the breath alcohol tester 102. The calibration station 100 may run off AC or DC power at a variety of voltage and current levels. In one implementation, the calibration station 100 runs off of 110/120 VAC power, but includes an AC-DC converter (not shown) either external to or within the calibration station 100. The calibration station 100 may further be selectively turned on and off using an on/off button 112. In other implementations, the on/off button 112 may be a switch or not included at all. For example, the calibration station 100 may automatically turn on when the breath alcohol tester 102 is mounted to the calibration station 100 and turn off when the breath alcohol tester 102 is removed from the calibration station 100.

The calibration station 100 still further includes a display 114 that communicates visual information to the user of the calibration station 100. Further, the display 114 may function as a touchscreen and accept user inputs. In other implementations, the calibration station 100 may communicate with an external display (not shown) such as that found in various smart phones, tablet computers, laptop computers, personal computers, and other computing devices. In other implementations, there are separate user input buttons (not shown) on the calibration station 100. The calibration station 100 may also include one or more internal or external speakers (not shown) that communicate audio information (e.g., bells, voice instructions, etc.) to the user. The calibration station 100 may also include one or more internal or external microphones (not shown) that accept audio input from the user (e.g., voice recognition commands). In another implementation, the breath alcohol tester 102 serves as a user input device to the calibration station 100, or vice versa. The information communicated to the user and received from the user via the display 114, the breath alcohol tester 102, the input button(s), the speaker(s), and/or the mic(s) is discussed in further detail below. In other implementations, the display 114 is omitted.

In one implementation, the calibration standard 124 is equipped with a radio-frequency identification (RFID) tag or a barcode/quick response (QR) code. Reading the RFID tag or barcode/quick response (QR) code using an appropriate scanner communicates information specific to the calibration standard 124 back to the calibration station 100, where in turn, the information may be communicated to the user via the display 114. This information may include calibration standard capacity, calibration standard alcohol concentration, calibration standard point of origin, calibration standard expiration date, etc. Further, instructions may be communicated to the user based on the status of the calibration standard (e.g., the tank is expired, please provide a new tank; the tank is low, please have a new tank ready; and the tank is full). The RFID or QR code may also be used to determine if an allowed calibration standard is used and automatically utilize the correct calibration tables that correspond to the calibration standard alcohol content. As a result, the calibration station 100 may utilize a variety of calibration standards from a variety of sources and with a variety of alcohol contents. Further, the calibration standard 124 may be connected internally to an electronic sensing device that is connected to and/or built into the calibration station 100 to perform the functions described above.

The calibration station 100 still further includes a communications and/or power cable 118 (e.g., a RS-232 cable) that electrically connects the breath alcohol tester 102 to the calibration station 100. The cable 118 provides power for charging the breath alcohol tester 102 and/or a communications medium for transmitting data (i.e., a data connection) between the calibration station 100 and the breath alcohol tester 102. In some implementations, no communications and/or power cable is connected to the breath alcohol tester 102. Further, the breath alcohol tester 102 may be charged separately from the calibration station 100.

Further, the breath alcohol tester 102 and/or the calibration station 100 may each include one or more wireless communication standards (e.g., Global Positioning System (GPS), Bluetooth, Wifi, infrared, etc.) to establish the data connection between the calibration station 100, the breath alcohol tester 102, and individuals responsible for the calibration station 100 and/or the breath alcohol tester 102 in various capacities (e.g., owners, users, manufacturers, maintenance personnel, and consumables (e.g., calibration standards) suppliers). Such communications may take place over the Internet or other data networks. For example, data collected by the breath alcohol tester 102 and/or the calibration station 100 may be communicated to a cloud computing server for safe, secure, and convenient storage and retrieval. This data may include calibration results, breath alcohol test results, calibration station usage, calibration standard expiration, calibration logs, tester use logs, and software updates, for example.

Still further, GPS receiver/transmitters may be incorporated into the breath alcohol tester 102 and/or the calibration station 100 in order to track the location of the units, recover lost/stolen units, and track unit locations relative to legal jurisdictional boundaries, for example. Still further, calibration settings and/or intervals may be automatically adjusted based on the physical location of the breath alcohol tester 102 and/or the calibration station 100 as determined by the GPS receiver/transmitter.

The calibration station 100 may also include a self-cleaning function that releases a burst of calibration fluid from the calibration standard 124 to clear the valves and regulators, tubes and hoses, and calibration fluid interface prior to calibration. In one implementation, this function is performed automatically on a time or number of uses schedule. In another implementation, the user requests that the calibration station 100 utilize the self-cleaning function. In yet another implementation, the calibration station 100 utilizes the self-cleaning function when it detects a potential problem using the pressure and mass flow rate sensors, for example.

The calibration station 100 may also include a calibration standard purging function. For example, when the calibration fluid runs low enough that it can no longer be used for reliable calibration of the breath alcohol tester 102, the calibration station 100 may automatically or upon user approval purge the remainder of the calibration fluid from the calibration standard 124 to render the calibration standard 124 safe for long term storage, transportation, recycling, and/or disposal. The calibration station 100 also includes a cable clasp 103 that is used to selectively secure and store the cable 118 when it is not connected to the breath alcohol tester 102.

Figure 2:
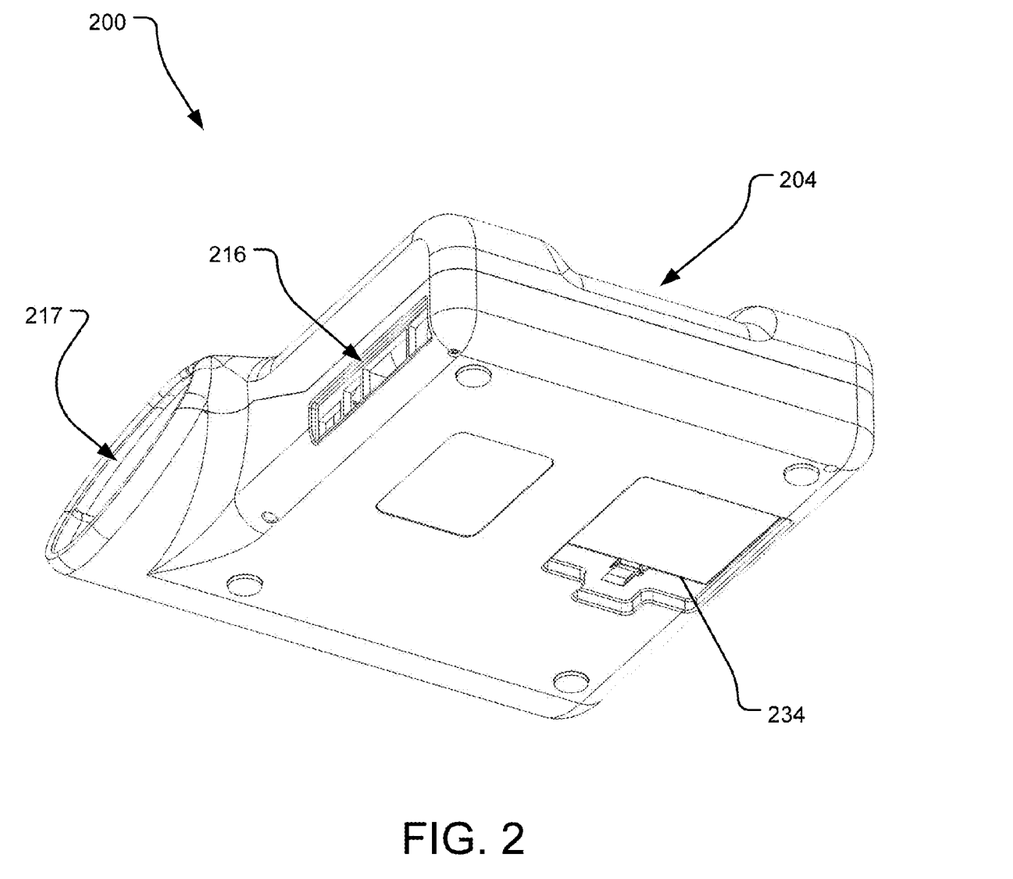
FIG. 2 is a second perspective view of an example calibration station.

FIG. 2 is a second perspective view of an example calibration station 200. A breath alcohol tester (not shown) is selectively mounted to the calibration station 200 using a device dock 204. The calibration station 200 includes a power supply port (not shown, see port 210 of FIG. 1) with which a user may connect a power supply cord (not shown) to directly power the calibration station 200 and/or charge one or more batteries (not shown) within the calibration station 200. The batteries may be permanently stored within the calibration station 200 or removable and replaceable. Further, the batteries may be located behind door 234. Other power supply sources may also be used (e.g., mechanical power, solar power, wind power, etc.) to power the calibration station 200.

The calibration station 200 still further includes communication ports 216 (e.g., USB, serial, Ethernet, HDMI, etc. ports), internal/external input devices, storage devices, and output devices. The communication ports 216 allow the calibration station 200 to establish a data connection to a local area network, the Internet, integrated or peripheral input devices (e.g., a mouse, a touchpad, etc.), integrated or peripheral output devices (e.g., a monitor, a printer, etc.), integrated or peripheral storage devices (e.g., a disc drive, a CD drive, a flash drive, a flash card, a tape drive, etc.), and so on. Further, the calibration station 200 may be configured to communicate with the local area network, the Internet, the peripheral devices, etc. via one or more wireless communication standards (e.g., Bluetooth, Wi-Fi, etc.). The data connection may permit software on the calibration station 200 to be updated, information stored within the calibration station 200 to be downloaded to another location, and/or information to be communicated between the user and the calibration station 200.

The calibration station 200 further includes an aperture 217 that receives a calibration standard (not shown). In one implementation, the calibration standard is a bottle or canister of a pressurized fluid with a precise known alcohol content percentage. The calibration standard is used as a comparison standard to check calibration and/or recalibrate (i.e., perform calibration processes) on the breath alcohol tester. The calibration fluid supply is inserted into the aperture 217 in the device dock 204 and screwed or otherwise secured in place and fluidly connected to the breath alcohol tester. The aperture 217 may be sized to receive a particular calibration standard bottle size or be adjustable to accept a variety of calibration standard bottle sizes. In other implementations, multiple apertures may be provided in the calibration station 200 for receiving multiple calibration standards.

Figure 3:
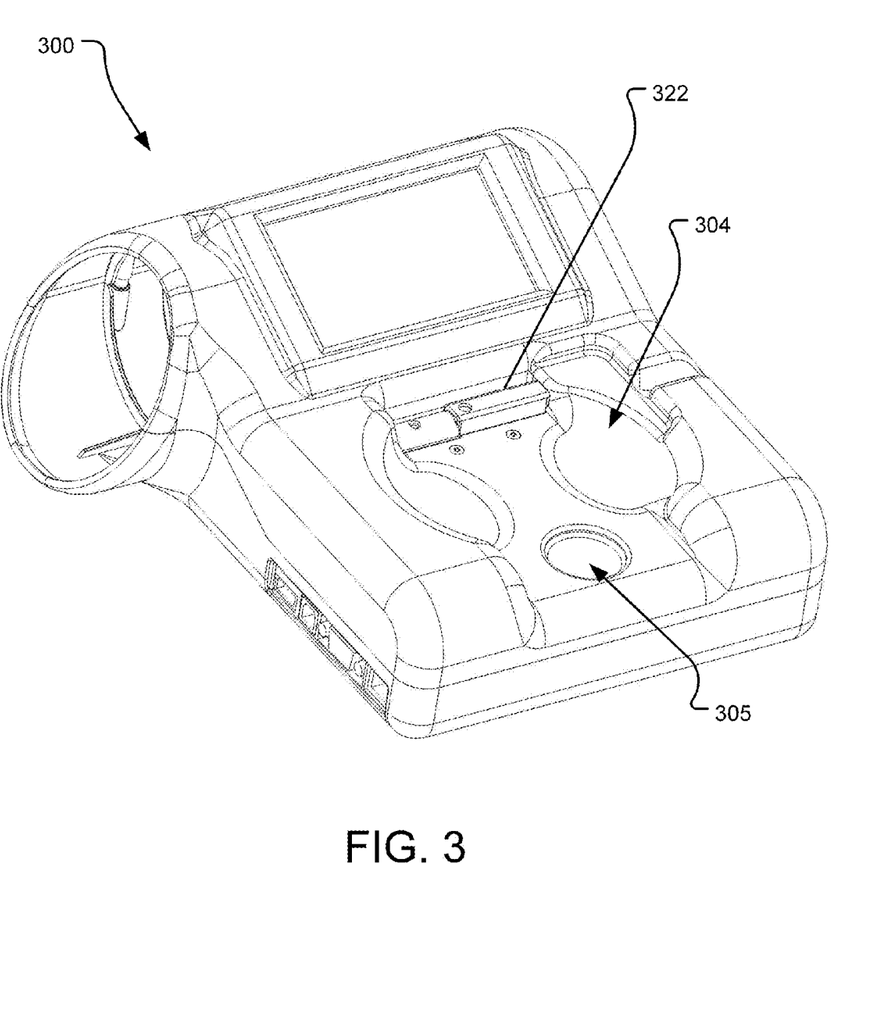
FIG. 3 is a third perspective view of an example calibration station.

FIG. 3 is a third perspective view of an example calibration station 300. A breath alcohol tester (not shown, see breath alcohol tester 102 of FIG. 1) is selectively mounted to the calibration station 300 using a device dock 304 as discussed in detail with regard to FIG. 1. Further, the device dock 304 may include a metallic or magnetic receptacle 305 that interfaces with a corresponding magnetic protrusion on the breath alcohol tester. This aids the alignment and secured fit of the breath alcohol tester to the calibration station 300. Further, the device dock 304 is contoured so that a user may easily grasp around the breath alcohol tester to remove it from the device dock 304. The device dock 304 may also include a docking sensor (e.g., a switch or a proximity sensor) that detects if the breath alcohol tester is properly docked within the device dock 304. If not, the calibration station 300 may alert a user via a visual or audio alarm.

The calibration station 300 may be mounted in a variety of orientations (e.g., on a generally horizontal surface like a desk or on a generally vertical surface like a wall). The calibration station 300 may also be configured to fit inside a travel case for portability (e.g., for use in the field or on the road). A magnetic interface between the calibration station 300 and the breath alcohol tester can allow the breath alcohol tester to remain properly docked in a variety of orientations of the calibration station 300. In other implementations, one or more hooks, clasps, doors, or other securing mechanisms may also be used to secure the breath alcohol tester in the device dock 304.

In other implementations, the calibration station 300 may include multiple device docks where multiple breath alcohol testers may be simultaneously mounted thereon. As a result, a singular calibration station 300 may be used to recharge and perform calibration processes on multiple breath alcohol testers simultaneously or in quick order. Further, the calibration station 300 may actively monitor the docked breath alcohol testers and perform calibration processes on them automatically as necessary or as desired and as discussed in detail herein.

The device dock 304 also includes a calibration fluid interface 322, which creates a fluid connection between the breath alcohol tester and a calibration standard (not shown) when the breath alcohol tester is properly mounted onto the calibration station 300. In one implementation, the calibration fluid interface 322 connects to the breath alcohol tester in the same manner and location as a mouthpiece for the breath alcohol tester. In some implementations, the calibration fluid interface 322 is identical to the mouthpiece of the breath alcohol tester. In other implementations, while the calibration fluid interface 322 is not identical to the mouthpiece of the breath alcohol tester, it closely replicates a user's breath path (e.g., tube inner form factor, e.g., shape and size) for accurate calibration.

In various implementations, the calibration fluid interface 322 may be attached to the breath alcohol tester first and then connected to the calibration station 300 via the device dock 304, or vice versa. Further, the calibration fluid interface 322 may be permanently affixed to or removable from the calibration station 300.

The device dock 304 may also include one or more electrical ports (not shown) which provide a power and/or a data connection between the breath alcohol tester and the device dock 304 when the breath alcohol tester is docked with the calibration station 300. In such an implementation, there are one or more corresponding electrical ports (not shown) on the rear of the breath alcohol tester.

Figure 4:
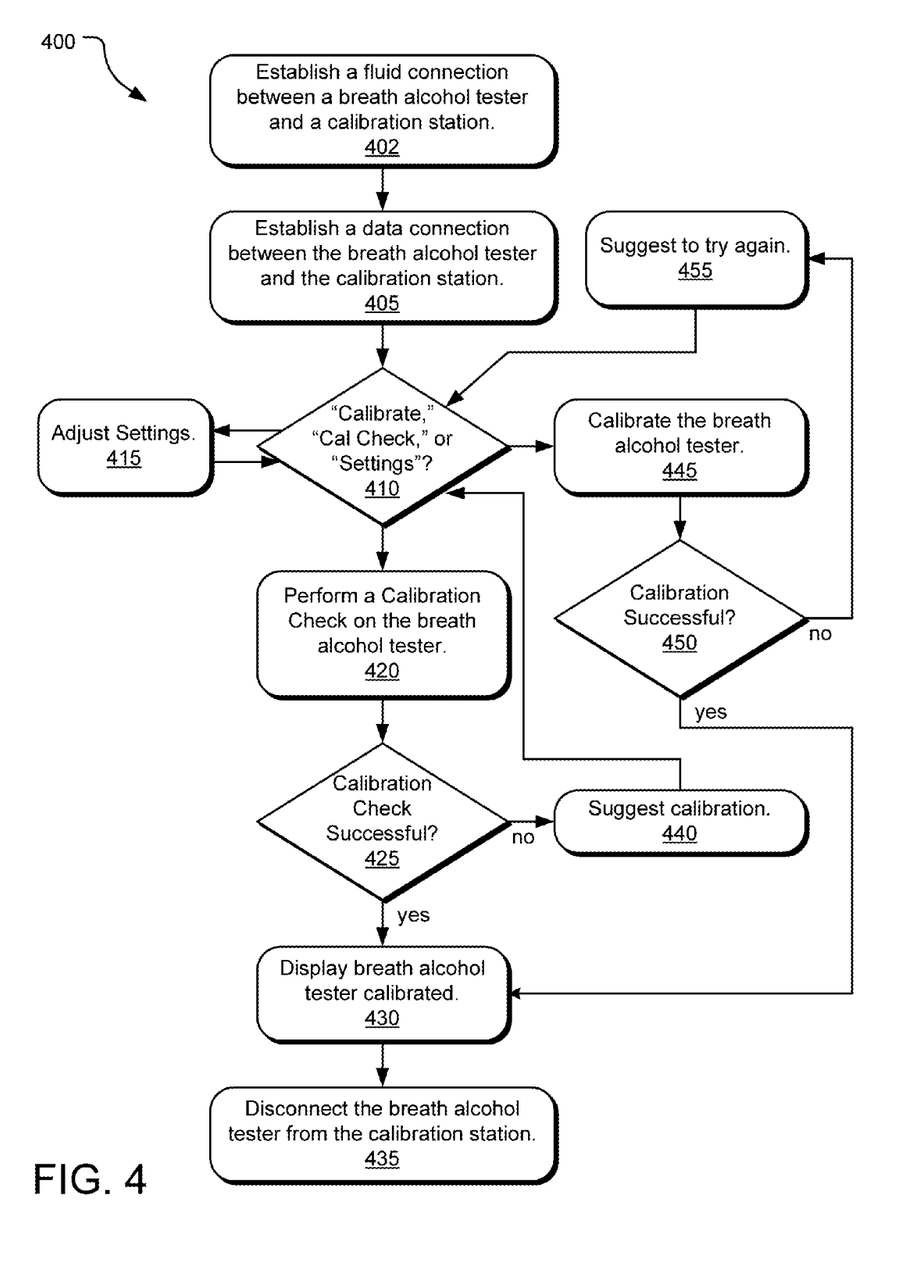
FIG. 4 illustrates example operations for performing a calibration process on a breath alcohol tester using a calibration station according to the presently disclosed technology.

FIG. 4 illustrates example operations 400 for performing a calibration process on a breath alcohol tester using a calibration station according to the presently disclosed technology. A first establishing operation 402 establishes a fluid connection between the breath alcohol tester and the calibration station. In one implementation, the breath alcohol tester is attached to the calibration station via a device dock that includes a calibration fluid interface. When the breath alcohol tester is docked within the device dock, the fluid connection is established via the calibration fluid interface. In other implementations, the calibration station does not include a device dock. In those implementations, the fluid connection between the breath alcohol tester and the calibration standard may be made by connecting a hose extending from the calibration standard directly to the breath alcohol tester, or vice versa.

A second establishing operation 405 establishes a data connection between the breath alcohol tester and the calibration station. In various implementations, the second establishing operation 405 may be accomplished by physically connecting a data cable between the breath alcohol tester and the calibration station or establishing a wireless data connection between the breath alcohol tester and the calibration station. Either upon completion of the second establishing operation 405 or upon turning the calibration station on, a main menu presents a user with various options for performing calibration processes on the breath alcohol tester. In one implementation, the user is presented with three options, "Calibrate," "Cal Check," and "Settings." In other implementations, the main menu may present greater or fewer options to the user. Further, the main menu may be displayed on a display of the calibration station, the breath alcohol tester, or both. Still further, in other implementations, the user is not presented with any options and the breath alcohol tester and/or calibration station performs the calibration processes automatically when the data and fluid connections are made or under remote user control.

The calibration station may receive various data from the breath alcohol tester when the data connection is established. For example, the calibration station may detect and compare the model number and software version of the breath alcohol tester with the model number and software version of the calibration station to determine compatibility. The calibration station and/or the breath alcohol tester may be configured to update its counterpart with the latest or necessary software to proceed with operations 400. Further yet, the calibration station may communicate calibration standard properties (e.g., state of fill, alcohol content, etc.) to the breath alcohol tester, or vice versa. Still further, the calibration station may detect ambient temperature, humidity, and barometric pressure conditions and store them for use as variables in the calibration processes. More specifically, the calibration station may detect the ambient barometric pressure and apply an adjustment factor dependent on the ambient barometric pressure to the calibration processes.

In one implementation, the calibration station and/or the breath alcohol tester may communicate to central technical support entity via a wireless (e.g., Wi-Fi, Bluetooth, or Cellular signal) or wired (e.g., Ethernet, PTSN) data connection. Central technical support may upload information (e.g., commands and software updates) to and/or download information from the calibration station and/or the breath alcohol tester. The central technical support may perform remote diagnostic procedures on the calibration station and/or the breath alcohol tester, for example, and retrieve the results of the diagnostic procedures from the calibration station and/or the breath alcohol tester. Central technical support may also be able to remotely enable or disable the calibration station and/or the breath alcohol tester or various features thereof.

Further, central technical support may use the data collected and stored on a cloud database to compare the operation of individual calibration station and/or the breath alcohol tester units in the field and recommend procedural adjustments to users/owners of units with a poor calibration/use record in order to optimize their use of the calibration stations. Still further, central technical support can use the collected data to predict a total cost of ownership and a timeline of cost to current and prospective owners based on aggregate costs experienced over the entire network of calibration stations and/or the breath alcohol testers. Further yet, central technical support may use the data collected and stored on the cloud database to make geographical and jurisdictional comparisons between different users operating different units in different areas. Further still, central technical support may use the data collected and stored on the cloud database to automate the reordering of calibration standards for the calibration stations.

In a decision operation 410, the user selects one of "Calibrate," "Cal Check," or "Settings" from the main menu to execute a calibration process by sending one or more commands to the breath alcohol tester. In other implementations, the calibration station is capable of performing calibration checks ("Cal Check"), but not full calibrations ("Calibrate") of the breath alcohol tester (such a calibration station is referred to as a "bump tester"). As a result, the user may only select one of "Cal Check" or "Settings" from the main menu of the reduced functionality bump tester calibration station. The calibration station/breath alcohol tester displays may also include battery status of the calibration station and/or breath alcohol tester and fill level/expiration date of the calibration standard. Still further, the calibration station may be connected to the Internet and automatically reorder or prompt the user to reorder a new calibration standard when the calibration standard is low, empty, nearing expiration, and/or expired.

If the user selects "Settings," the user is redirected to one or more additional menus where the user can adjust the settings of one or both of the calibration station and the breath alcohol tester. In an adjusting operation 415, the user adjusts one or more of the calibration station and/or breath alcohol tester settings using user inputs into the one or more additional menus. For example, the user may be presented with options on the calibration station/breath alcohol tester displays to check and/or adjust "General Settings" (e.g., date/time, date format, time format, and time zone, etc.), "Dry Gas settings" (e.g., alcohol concentration level, expiration date, tank size, life status, and barometric pressure, etc.), and "About" (e.g., display serial number, software version, model number, last recalibration date/time, last calibration check date/time, software updates, etc.). In other implementations, the "Settings" menus may present greater or fewer options to the user, or may be absent all together.

If the user selects "Cal Check," performing operation 420 performs a calibration check on the breath alcohol tester. In one implementation, the calibration station automatically performs the performing operation 420 without any additional input from the user. The performing operation 420 may include one or more of verifying sufficient calibration fluid quantity and pressure for the calibration check, changing the breath alcohol tester to a calibration check mode, opening the fluid connection (e.g., opening a valve) between the calibration standard and the breath alcohol tester, waiting an appropriate time (e.g., 3 seconds) for the calibration fluid to reach the breath alcohol tester, taking a sample of the released calibration fluid, closing the fluid connection (e.g., closing the valve) between the calibration standard and the breath alcohol tester, and analyzing the alcohol content of the calibration fluid sample. In various implementations, the aforementioned wait time may range from 1 to 14 seconds. The calibration check is referred to herein as an example calibration process.

Further, the menu may display instructions to the user to wait for completion of the calibration check and/or display an estimated time until completion of the calibration check. Upon completion of the calibration check, decision operation 425 determines if the breath alcohol tester passed the calibration check (i.e., the detected alcohol content of the calibration standard is within a predetermined tolerance from the actual alcohol content of the calibration standard. In one implementation, the calibration station automatically performs the decision operation 425 without any additional input from the user and outputs via the display whether the calibration check was successful or not.

If the calibration check on the breath alcohol tester was successful, displaying operation 430 informs the user that the breath alcohol tester is calibrated. In a disconnecting operation 435, the user may disconnect the breath alcohol tester from the calibration station and put the breath alcohol tester into service. In some implementations, the calibration station may instruct the user when it is appropriate to perform the disconnecting operation 435 by displaying a message to the user.

If the calibration check of the breath alcohol tester was not successful, suggestion operation 440 displays to the user a message suggesting that the user recalibrate the breath alcohol tester. The suggestion operation 440 may be performed by the calibration station and then after a predetermined time or after user acknowledgment of the message, the calibration station returns to the main menu again presenting the user the "Calibrate," "Cal Check," and "Settings" options (see decision operation 410). Further, the suggestion operation 440 may automatically trigger recalibration of the breath alcohol tester.

If the user selects "Calibrate," calibration operation 445 recalibrates the connected breath alcohol tester. In one implementation, the calibration station automatically performs the calibration operation 445 without any additional input from the user. The calibration operation 445 may include one or more of verifying sufficient calibration fluid quantity and pressure for recalibration, changing the breath alcohol tester to a calibration mode, opening the fluid connection (e.g., opening a valve) between the calibration standard and the breath alcohol tester, waiting an appropriate time (e.g., 3 seconds) for the calibration fluid to reach the breath alcohol tester, taking a sample of the released calibration fluid, closing the fluid connection (e.g., closing the valve) between the calibration standard and the breath alcohol tester, analyzing the alcohol content of the calibration fluid sample, and adjusting the calibration state of the breath alcohol tester to match the known alcohol content of the released calibration fluid. In various implementations, the aforementioned wait time may range from 1 to 14 seconds.

Further, the menu may display instructions to the user to wait for completion of the calibration operation 445 and/or display an estimated time till completion of the calibration operation 445. Upon completion of the calibration operation 445, decision operation 450 determines if the breath alcohol tester was successfully calibrated (i.e., an additional calibration check may determines if the detected alcohol content of the calibration standard is within a predetermined tolerance (e.g., 0.005%) from the actual alcohol content of the calibration standard). In one implementation, the calibration station automatically performs the decision operation 450 without any additional input from the user and outputs via the display whether the calibration was successful or not.

If the calibration operation 445 was not successful, suggestion operation 440 displays to the user a message suggesting that the user try to calibrate the breath alcohol tester again. The suggestion operation 440 may be performed by the calibration station and then after a predetermined time or after user acknowledgment of the message, the calibration station returns to the main menu presenting use the "Calibrate," "Cal Check," and "Settings" options (see decision operation 410). In other implementations, the suggestion operation 455 may suggest that the user check and/or replace the calibration standard.

If the calibration operation 445 was successful, displaying operation 430 displays to the user that the breath alcohol tester is calibrated. In a disconnecting operation 435, the user disconnects the breath alcohol tester from the calibration station and may put the breath alcohol tester into service. In some implementations, the calibration station may instruct the user when it is appropriate to perform the disconnecting operation 435 by displaying a message to the user.

Further, the calibration station may turn off or go into a low power state if not used within a predetermined time (e.g., 15 minutes). Still further, the calibration station may include password protection to limit access to authorized users. Further yet, the calibration station may store a number of previous calibrations or calibration checks (e.g., a log of up to 50 previous recalibrations or calibration checks). This data may be stored within the calibration station, within the breath alcohol tester, and/or output to a local area network, the Internet, a printer, or an external storage device, for example.

One or both of the calibration station and the connected breath alcohol tester may perform each of the operations 400. In one implementation, the calibration station may include none or very little computing circuitry with the majority of the operations 400 performed by the connected breath alcohol tester that contains the majority of the computing circuitry. While the embodiments above are discussed with specific reference to a breath alcohol tester, the disclosed calibration station may be used to calibrate other testing devices (e.g., a drug or alcohol tester using breath, blood, or urine analysis), including any volatile compound testing device.

The embodiments of the invention described herein are implemented as logical steps in one or more computer systems. The logical operations of the present invention are implemented (1) as a sequence of computer processor-implemented steps executing in one or more computer systems and (2) as interconnected machine or circuit modules within one or more computer systems. The implementation is a matter of choice, dependent on the performance requirements of the computer system implementing the invention. Accordingly, the logical operations making up the embodiments of the invention described herein are referred to variously as operations, steps, objects, or modules. Furthermore, it should be understood that logical operations may be performed in any order, unless explicitly claimed otherwise or a specific order is inherently necessitated by the claim language.

The above specification, examples, and data provide a complete description of the structure and use of exemplary embodiments of the invention. Since many embodiments of the invention can be made without departing from the spirit and scope of the invention, the invention resides in the claims hereinafter appended. Furthermore, structural features of the different embodiments may be combined in yet another embodiment without departing from the recited claims.

What is claimed is:

1. A method of performing a calibration process on a breath alcohol tester using a calibration station, the method comprising:
    establishing a data connection between the breath alcohol tester and the calibration station;
    sending a command from the calibration station to the breath alcohol tester;
    executing the calibration process on the breath alcohol tester in response to the command;
    opening a fluid connection between the breath alcohol tester and a calibration standard in response to execution of the calibration process and
    controlling the breath alcohol tester via circuitry on the calibration station.

2. The method of claim 1, wherein the calibration process includes one or both of a calibration check and a recalibration of the breath alcohol tester.

3. The method of claim 1, wherein the calibration process includes a recalibration and a subsequent calibration check of the breath alcohol tester.

4. The method of claim 1, wherein the calibration process includes automatically actuating a valve on a line fluidly connecting the breath alcohol tester to the calibration station.

5. The method of claim 1, further comprising:
    receiving data from the breath alcohol tester to the calibration station.

6. The method of claim 5, wherein the data includes one or more of ambient barometric pressure, a tester model number, a tester serial number, a tester software version, a previous calibration log, and a previous test log.

7. The method of claim 1, wherein the command includes one or both of running a recalibration and installing a software update on the breath alcohol tester.

8. The method of claim 1, further comprising:
    detecting a physical connection between the breath alcohol tester and the calibration station, wherein opening the fluid connection between the breath alcohol tester and the calibration standard is further in response to detecting the physical connection between the breath alcohol tester and the calibration station.

9. The method of claim 1, further comprising:
    receiving calibration standard data from the calibration standard.

10. The method of claim 9, wherein the calibration standard data includes one or more of calibration standard capacity, calibration standard pressure, calibration standard alcohol concentration, calibration standard point of origin, and calibration standard expiration date.

11. The method of claim 1, wherein the breath alcohol tester is controlled by the calibration station via the data connection.

12. The method of claim 1, further comprising:
    closing the fluid connection in response to a signal that the calibration process is complete.

13. The method of claim 12, wherein a time elapsed between opening the fluid connection between the breath alcohol tester and the calibration standard and closing the fluid connection ranges from 1 to 14 seconds.

14. The method of claim 1, further comprising:
    checking compatibility between the breath alcohol tester and the calibration station prior to executing the calibration process.

15. The method of claim 1, further comprising:
    outputting a result of the calibration process to a display on the calibration station.

16. The method of claim 1, wherein the calibration process is performed by a computer processor and opening the fluid connection between the breath alcohol tester and the calibration standard is performed in response to instructions from the computer processor.

17. A method of performing a calibration process on a breath alcohol tester using a calibration station, the method comprising:
    establishing a fluid connection between the breath alcohol tester and a calibration standard with a known alcohol content;
    establishing a data connection between the breath alcohol tester and the calibration station;
    sending a command from the calibration station to the breath alcohol tester;
    executing the calibration process on the breath alcohol tester in response to the command thereby putting the breath alcohol tester under control of the calibration station;

opening the fluid connection between the breath alcohol tester and a calibration standard in response to execution of the calibration process;
detecting the alcohol content of the calibration standard using the breath alcohol tester;
closing the fluid connection between the breath alcohol tester and the calibration standard in response to detecting the alcohol content of the calibration standard;
comparing the detected alcohol content with the known alcohol content of the calibration standard; and
outputting a result of comparing the detected alcohol content with the known alcohol content to a display on the calibration station.

18. The method of claim 17, further comprising:
recalibrating the breath alcohol tester by equating the detected alcohol content to the known alcohol content of the calibration standard.

19. The method of claim 17, further comprising:
measuring an ambient barometric pressure, wherein detecting the alcohol content of the calibration standard is dependent on the measured ambient barometric pressure.

20. The method of claim 17, wherein the known alcohol content of the calibration standard is less than 1100 parts per million of ethanol.

21. The method of claim 1, wherein the command includes running a calibration check, wherein the calibration check includes one or more of verifying sufficient calibration fluid quantity and pressure for the calibration check, changing the breath alcohol tester to a calibration check mode, opening the fluid connection between the calibration standard and the breath alcohol tester, waiting an appropriate time for the calibration fluid to reach the breath alcohol tester, taking a sample of the released calibration fluid, closing the fluid connection between the calibration standard and the breath alcohol tester, and analyzing the alcohol content of the calibration fluid sample.

22. The method of claim 1, further comprising:
attaching the breath alcohol tester to the calibration station via a device dock that includes a calibration fluid interface.

23. A calibration comprising:
a user input interface configured to receive an input command for a calibration process from a user;
circuitry on the calibration station configured to establish a data connection between a breath alcohol tester and the calibration station, send the input command from the calibration station, send the input command from the calibration station to the breath alcohol tester, execute the calibration process on the breath alcohol tester in response to the input command, and control the breath alcohol tester;
a calibration fluid interface configured to fluidly connect a calibration standard to the breath alcohol tester; and
a valve configured to open the fluid connection between the calibration standard and the breath alcohol tester in response to execution of the calibration process on the breath alcohol tester.

24. The calibration station of claim 23, wherein the calibration process includes one or both of a calibration check and a recalibration of the breath alcohol tester.

25. The calibration station of claim 23, further comprising:
a device dock configured to receive the breath alcohol tester onto the calibration station and establish the calibration fluid interface between the breath alcohol tester and the calibration station.

26. The calibration station of claim 25, wherein the device dock includes a docking sensor configured to indicate that the breath alcohol tester is properly received onto the calibration station.

27. The calibration station of claim 23, further comprising:
a display that outputs a result of the calibration process to the user.

28. The calibration station of claim 23, further comprising:
one or more barometric pressure sensors that measure an ambient barometric pressure, wherein the calibration process is dependent on the measured barometric pressure.

* * * * *

UNITED STATES PATENT AND TRADEMARK OFFICE
CERTIFICATE OF CORRECTION

PATENT NO.         : 9,562,883 B2
APPLICATION NO.    : 13/957180
DATED              : February 7, 2017
INVENTOR(S)        : Knott et al.

Page 1 of 1

It is certified that error appears in the above-identified patent and that said Letters Patent is hereby corrected as shown below:

On the Title Page

At Item (72) Inventors:
At Line 2 delete "US" after Silverman and insert --Denver--.

Signed and Sealed this
Thirty-first Day of July, 2018

Andrei Iancu
*Director of the United States Patent and Trademark Office*